(12) United States Patent
Silver et al.

(10) Patent No.: US 11,105,490 B1
(45) Date of Patent: Aug. 31, 2021

(54) LIGHTING DEVICE WITH PROTECTIVE LIGHT MANAGEMENT

(71) Applicant: Designs for Vision, Inc., Bohemia, NY (US)

(72) Inventors: Samantha A. Silver, New York, NY (US); Matthew A. Kenyon, St. James, NY (US); Matthew D. Siedman, Babylon, NY (US); Kenneth N. Braganca, Sayville, NY (US)

(73) Assignee: Designs for Vision, Inc., Bohemia, NY (US)

( * ) Notice: Subject to any disclaimer, the term of this patent is extended or adjusted under 35 U.S.C. 154(b) by 0 days.

(21) Appl. No.: 16/795,547

(22) Filed: Feb. 19, 2020

Related U.S. Application Data

(60) Provisional application No. 62/863,196, filed on Jun. 18, 2019.

(51) Int. Cl.
| | | |
|---|---|---|
| *F21V 11/18* | (2006.01) | |
| *F21V 17/02* | (2006.01) | |
| *F21V 14/08* | (2006.01) | |
| F21V 21/084 | (2006.01) | |

(52) U.S. Cl.
CPC .......... *F21V 11/183* (2013.01); *F21V 14/085* (2013.01); *F21V 17/02* (2013.01); *F21V 21/084* (2013.01)

(58) Field of Classification Search
CPC ...... F21V 11/183; F21V 17/02; F21V 14/085; F21V 21/084
See application file for complete search history.

(56) References Cited

U.S. PATENT DOCUMENTS

| | | | | |
|---|---|---|---|---|
| 2,286,353 A | * | 6/1942 | Ehehalt, Jr. | E06B 7/30 359/636 |
| 2,632,252 A | * | 3/1953 | Blais, Sr. | F41G 1/383 359/511 |
| 4,666,280 A | * | 5/1987 | Miyawaki | G03B 7/16 396/175 |
| 5,115,382 A | * | 5/1992 | Smith | F21L 4/06 2/906 |
| 6,076,891 A | * | 6/2000 | Bernhardt | A47C 1/03 297/411.31 |
| 7,690,806 B2 | | 4/2010 | Feinbloom | |
| 8,215,791 B2 | | 7/2012 | Feinbloom | |
| 8,851,709 B2 | | 10/2014 | Feinbloom | |
| 9,226,372 B2 | | 12/2015 | Johnson | |
| 9,791,138 B1 | | 10/2017 | Feinbloom | |
| 9,968,417 B2 | | 5/2018 | Johnson | |
| 10,132,483 B1 | | 11/2018 | Feinbloom | |
| 10,240,769 B1 | | 3/2019 | Braganca | |

(Continued)

*Primary Examiner* — Rajarshi Chakraborty
*Assistant Examiner* — Glenn D Zimmerman
(74) *Attorney, Agent, or Firm* — Law Office of Carl Giordano, PC

(57) ABSTRACT

A light management device comprising a protective light cap or cover is disclosed that provides for the blockage or allowance of designated wavelengths from being inadvertently being viewed by persons or being projected onto an external surface. The protective light cap or cover is pivotable connected to a lighting source to allow the cap to be positioned over the light source and moved away from the light source. The protective light cap is retained in an open position that allows the light source to be viewed, by one of a magnetic catch or a physical catch.

20 Claims, 10 Drawing Sheets

(56) References Cited

U.S. PATENT DOCUMENTS

| | | |
|---|---|---|
| 10,352,543 B1 | 7/2019 | Braganca |
| 2003/0137547 A1* | 7/2003 | Brown ...................... G06F 3/14 715/865 |
| 2011/0170280 A1* | 7/2011 | Soto ...................... F21V 21/084 362/105 |
| 2016/0327429 A1* | 11/2016 | Vienot ...................... G01J 1/42 |
| 2018/0217403 A1* | 8/2018 | Foss ......................... G02C 5/08 |

\* cited by examiner

LIGHTING DEVICE WITH PROTECTIVE LIGHT MANAGEMENT

CLAIM OF PRIORITY

This application claims, pursuant to 35 USC 119, priority to and the benefit of the earlier filing date, of that provisional application afforded Ser. No. 62/863,196 and filed on Jun. 18, 2019, the contents of which are incorporated by reference, herein.

FIELD OF THE INVENTION

This invention relates to the field of lighting and more particularly to a safety apparatus for the prevention of eye damage caused by the inadvertent viewing of light harmful to the eyes.

BACKGROUND OF THE INVENTION

Head-mounted lighting devices are typically used in dental, medical and/or surgical fields to allow practitioners (i.e., dentist, doctor) to have a light applied directly to the area where the practitioner is viewing. Head-mounted lighting devices are advantageous over overhead type lighting devices as the practitioner's shadow is not projected onto the work area. In many cases, the projected light is not necessarily white light but rather may be of wavelengths (e.g., ultraviolet (UV) wavelength band) that are harmful when viewed without protective lens. This is particularly true for dentistry where lights in the UV band are used, for example in specialized industries. For examiner in the dental art, the use of wavelengths that may be harmful to a user's eyes may be used in curing epoxies or similar materials used for repair or improving on a patient's teeth.

Generally, a practitioner (such as a dentist) and their assistant are required to use protective eyewear to prevent stray UV light from entering their eyes. However, when the protective eyewear is worn, neither the dentist nor the assistants are able to see the UV light as the protective eyewear removes (i.e., filters out) the harmful UV light from the light that is seen by the dentist and the assistant.

Thus, it is possible that one or more of the practitioner and/or assistant removes their protective eyewear before the harmful UV light is turned off, and if viewed may cause damage to the viewer's eyes. Similarly, a high powered white light or Infra-Red light may be viewed by personal that fail to have proper eye protection. Such high powered light similarly may cause damage to the viewer's eyes.

Hence, there is a need in the industry for providing a light management system for managing the outputting of light that may be harmful to personal who may inadvertently view to light to prevent damage to that person's eyes.

SUMMARY OF THE INVENTION

In accordance with the principles of the invention, a light management device is applied to a lamp or light assembly that may be used to block light in a light range that may be harmful to personal who view the light. For example, UV light is known to be harmful to persons viewing the UV light and such a light management device is necessary to prevent damage to the eyes of such persons.

In accordance with the principles of the invention, a light management device is applied to a lamp assembly that may be used to filter light in a light range that may be harmful to personal who view the light such that the harmful light may not be viewed by personal.

In accordance with the principles of the invention, a light management device is applied to a lamp assembly wherein the light management system controls the output of a light such that the light having harmful light wavelengths may either be viewed without the unharmful wavelength range or may be blocked from being viewed.

In accordance with the principles of the invention, a light management device is applied to a lamp assembly that may control the output of a light having a range of wavelengths that are harmful to the eyes of those viewing the light. o

BRIEF DESCRIPTION OF DRAWINGS

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

It is to be understood that the figures and descriptions of the present invention described herein have been simplified to illustrate the elements that are relevant for a clear understanding of the present invention, while eliminating for purposes of clarity, many other elements. However, because these omitted elements are well-known in the art, and because they do not facilitate a better understanding of the present invention, a discussion of such elements is not provided herein. The disclosure herein is directed also to variations and modifications known to those skilled in the art.

DETAILED DESCRIPTION

Figure 1:
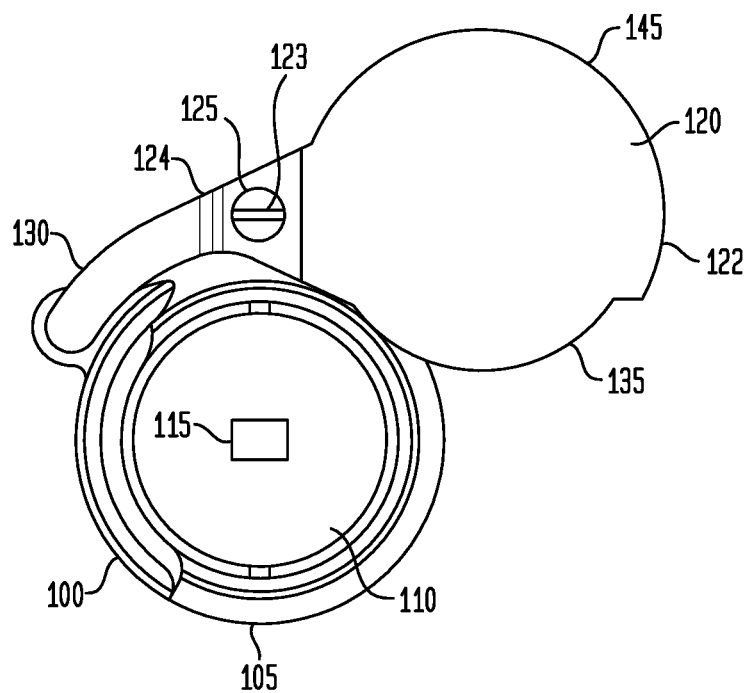
FIG. 1 illustrates front view of a first exemplary embodiment of a light management device shown in a first position.

FIG. 1 illustrates a front view of a first exemplary embodiment of a lighting device management 100 and light management system 120 suitable for being attached to head mounting device such as eyewear, headband, headset, clothing, etc.

Light management device 100 comprises a housing 105 containing at least one lighting source 115, therein, and a lens 110 positioned on a distal end of housing 105. Light emitted by the least one lighting source 115 is allowed to pass through lens 110 so as to be projected onto an external surface (not shown). Lighting source 115 may be a Light Emitting Diode (i.e., a semiconductor diode that illuminates when a voltage is applied. In addition, as used, herein, the term Light Emitting Diode (LED) may represent, for example, a, super bright or super luminance semiconductor diode—(i.e., a non-lasing LED or other similar non-lasing devices) or may represent a semiconductor diode laser (i.e., a lasing LED)) that may emit light in one or more wavelength ranges. Lighting source 115 may be a lasing diode that outputs a coherent light in one or more wavelength ranges or a non-lasing diode (i.e., super conductive diode) that outputs a non-coherent light in one or more wavelength ranges. In one aspect, when light generated by the lighting source 115 is in the UV (Ultra-Violet) light range (i.e., wavelengths less than approximately 500 mn), the user, and those around the user, require eye protection from the harmful effects of the UV light on the eye. Similarly, when the light generated by the at least one lighting source 115 is a high intensity visible light, those around the user may need be protected from the high intensity visible light being directed directly into their eyes.

In accordance with the principles of the invention, light management system 120 is incorporated onto a distal end of housing 105 to manage the emission of the light generated by the at least one lighting source 115 contained within lighting device 100.

Specifically, the light management system 120 comprises a cover plate, a cover surface or a cover cap 122, a control section 130 and a passthrough 124 positioned between the cover plate 122 and control section 130. Passthrough 124 provides a means for attaching light management device 120 to the distal end of housing 105.

In one exemplary embodiment of the invention, an attachment means that is substantially cylindrical (e.g., a screw or pin or rivet) 123 may be inserted through passthrough 124 to retain light management device 120 with respect to housing 105, as will be discussed.

Passthrough 124, in combination with attachment means 123, forms a pivot point 125 that allows light management device 120 to be selectively positioned away from the least one lighting source 115 or in front of at least one lighting source 115.

Light management system (or device) 120 may be attached to housing 105 using a screw, pin or rivet 123 extending through passthrough 124 of light management device 120, wherein screw, pin or rivet (i.e., an essentially cylindrical object) 123 provides for an attachment (not shown) to housing 105. In this case, passthrough 124, which includes an internal screw thread may be also be a blind passthrough (i.e., entry on one side but no exit on a second side). In accordance with the principles of the invention, screw or pin 123 may include a screw thread that allows for a screw thread attachment to housing 105. In another aspect, wherein the attachment means 123 may be a pin that may have a force fit, snap fit or a pressure fit attachment connection to housing 105. In another aspect, wherein the attachment means 123 may be a rivet, the rivet may extend through passthrough 124 and includes flattened ends that retain rivet 123 in place.

Figure 2:
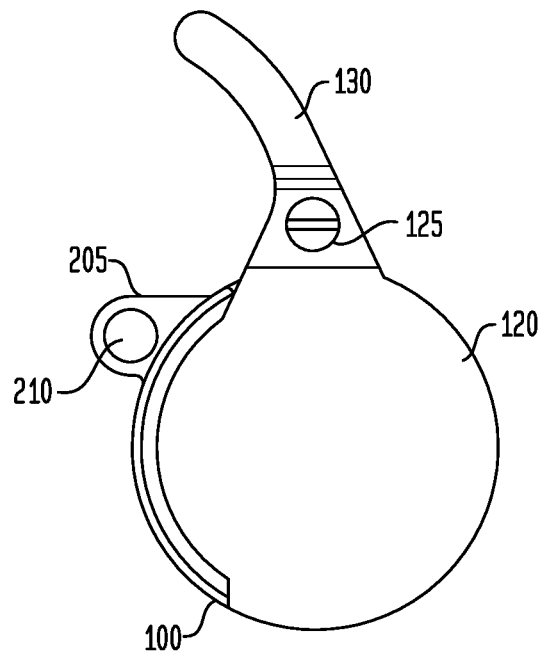
FIG. 2 illustrates the first exemplary embodiment of the light management device shown in FIG. 1 in a second position.

In one aspect of the invention, light management device 120 may pivot or rotate about screw (pin, rivet) 123 to change an orientation of light management device 120 from a first position (shown) to a second position (see FIG. 2). In the first position (shown), the at least one lighting source 115 is viewable through lens 110 and the light generated by at least one lighting source 115 may be emitted from housing 115. Whereas, in the second (or closed) position the at least one lighting source 115 is not viewable. In this second (closed) position, light generated by the at least one lighting source 115 within housing 105 is not visible to a person who may be opposite to, and who may inadvertently view, the output of lighting device 100.

The light management system 120 further includes a control section 130, which is shown as a lever. Lever 130 allows for the manipulation of light management device 120 to be pivoted about pivot point 125 from the first (open) position (FIG. 1) to the second (closed) position (FIG. 2) or from the second (closed) position to the first (open) position.

Although, the illustrated embodiment discloses a control section 130 as being a lever that extends from the plate section 122, it would be recognized light management device 120 may be constructed without control section 130 and that operation of light management device 120 may be performed by a direct contact, by a user, with cover plate 122 section of light management device 120. For example, cover plate may include an indentation into which an object (i.e., a finger) may be inserted. The inserted object may then be used to move the light management device 120 from a closed position to an open position. In another aspect of the invention, the control section 130 may be an extended knob that provides for the movement of cover plate 122.

FIG. 2 illustrates a front view of lighting device 100, wherein the light management device 120 is configured to inhibit light emitted by the at least lighting source 115 within housing 105 from exiting housing 105. In this illustrated aspect, light management device 120 is placed in a second (closed) position wherein light management device 120 is pivoted about pivot point 125 such that light management device 120 is placed in the path of light emitted by at least one light source 112 in which case light (i.e., UV, visible, infra-red) emitted by the at least one lighting source 115 (not shown) within housing 105 is blocked from being viewed or projected onto an external surface.

In this illustrated second (closed) position, control section 130 is positioned in a substantially vertical position with respect to housing 105. However, it would be recognized that the positioning of control section 130 is dependent on the orientation of control section 130 with respect to housing 105 and that the illustrated embodiment is merely representative of the construction of light management device 120 including control section 130. That is, FIG. 1 illustrates light management device 120 and control section 130 are in a substantially horizontal plane with respect to housing 105. When an orientation of light management device 120 is changed from a substantially horizontal plane to a substantially vertical plane (FIG. 2), the change in orientation of lever 130 is substantially the same as that of the plate section 122 of light management device 120.

In accordance with the principles of the invention, housing 105 may further include a housing extension 205 extending from housing 105. Housing extension 205, in this illustrated embodiment, includes magnet 210. Magnet 210 is configured to interact with control section 130. For example, and returning to FIG. 1, control section 130 is positioned opposite magnet 210 (not shown) to retain control section 130 in the illustrated first position. Accordingly, the magnetic force exerted by magnet 210 is sufficient to retain control section 130 in a fixed position by counter-balancing the weight of cap plate 122 such that light management device 120 remains in the illustrated open position. In this case, the illustrated position is referred to as an "open position" as the light emitted by lighting source 115 is viewable by persons opposite housing 105 or projected onto an external surface.

In accordance with the principles of the invention, when a force is applied to control section 130 that is sufficient to overcome the magnetic force of magnet 210, light management device 120 pivots about pivot point 125 from the illustrated first position (FIG. 1) to a second position (FIG. 2) (referred to as a closed position).

In this closed position, light emitted by lighting source 115 is no longer visible to persons opposite housing 105 or projected onto an external surface.

Figure 3:
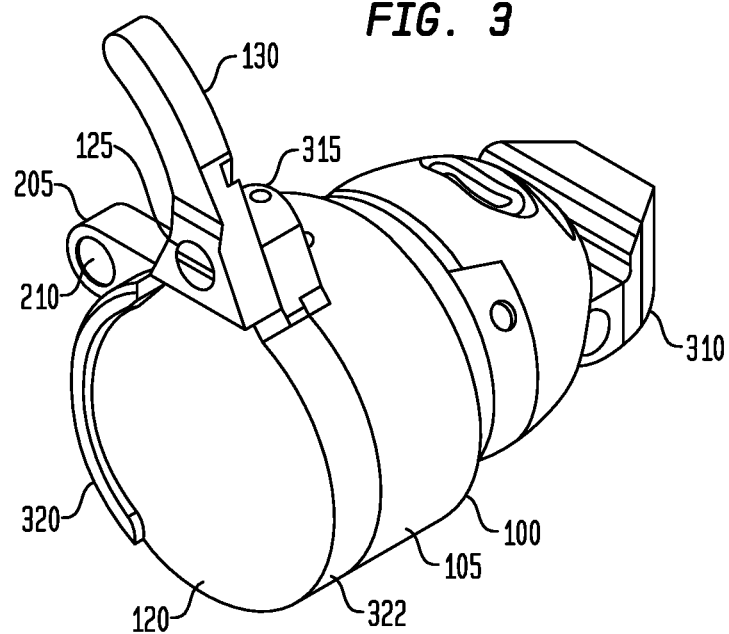
FIG. 3 illustrates a prospective view of the first exemplary embodiment of the light management device shown in FIG. 1.

FIG. 3 illustrates a prospective view of light device 100 including light management device 120 in a second (or closed) position that prevents the viewing of light generated by lighting source 115.

In this illustrated embodiment, housing extension 205 containing magnet 210 is shown oriented substantially in a horizontal plane with respect to housing 105 and is substantially perpendicular to control section 130. Further illustrated is cover attachment section 315 extending from a distal end of housing 105 through which attachment means (screw, pin or rivet) 123 retains light management device 120 to housing 105.

For example, when attachment means 123 is a screw, attachment section 315 may include a threaded passthrough 330 (FIG. 4) that captures the threads of screw 123 to retain light management device 120 to distal end of housing 105. Light management device 120 may then pivot or rotate about the cylindrical shaft of screw 123. Alternatively, when attachment means 123 is a pin, then passthrough 330 of cover attachment section 315 may provide for a snap fit, a snug-fit, or a pressure-fit connection that captures pin 123 to retain light management device 120 onto the distal end of housing 105. Light management device 120 may then pivot or rotate about the cylindrical shaft of pin 123. Similarly, when attachment means 123 is a rivet, then passthrough 330 of attachment section 315 may allow rivet 123 to pass completely through passthrough 330. The ends of the rivet 123 may then be flattened to retain light management device 120 to housing 105. Light management device 120 may pivot or rotate about the cylindrical shaft of rivet 123.

In accordance with one aspect of the invention, a stop channel 320 may extend partially along a circumference of the distal end of housing 105. Stop channel 320 comprises an extension of the distal end of housing 105 that forms a channel into which edge 135 (FIG. 1) of the cover plate section 122 of light management device 120 fits. In this illustrated aspect of the invention, when cover plate 122 is in the second or closed position, edge 135 of cover cap 122 is contained with stop channel 320.

Stop channel 320, hence, provides a means for retaining light management device 120 in a substantially light tight configuration with respect to housing 105, wherein light wavelengths generated by at least one lighting source 115 are not viewable through a crack or slit between edge 135 and housing 105.

Stop channel 320 further limits the extent to which light management device 120 moves when moving into the closed position and from moving when in the closed position.

Further illustrated is housing attachment section 310 at a proximal end of housing 105. Housing attachment section 310 allows for the attachment of lighting device 100 onto another element (e.g., an eyewear, a headband, or head gear having a matching connection). In one exemplary embodiment, attachment means 310 may include a T-slot connection that allows lighting device 100 to be removable from an eyewear, for example, that includes a matching connection. Additional, lighting device 100 including light management system 120 may be attached to other devices, such as clothing or racks using a similar T-slot connection.

However, as will be discussed, with regard to FIGS. 15 and 16, lighting device 100 may be connected to a lighting assembly with or without the use of attachment section 310.

Figure 4:
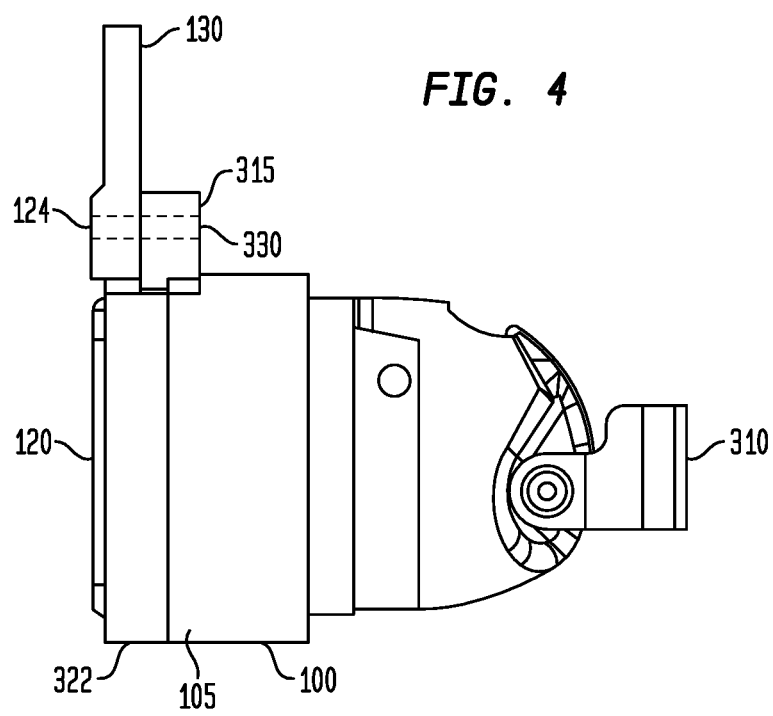
FIG. 4 illustrates a side view of the first exemplary embodiment of the light management device shown in FIG. 1.

FIG. 4 illustrates a side view of the lighting device 100 shown in FIG. 1. In this illustrated view, light management device 120, illustrated in a closed position, is retained over a front facing surface (i.e., the distal end) of housing 105.

Further illustrated is cover attachment section 315 extending from the distal end of housing 105. Cover attachment section 315, includes passthrough 330, that provides a means to capture attachment means 123 and retain light management device 120 to distal end of housing 105.

Although attachment section 315 is shown extended from the distal end of housing 105, it would be recognized that attachment section 315 may be incorporated into the distal end of housing 105. For example, a thickness of the distal end of housing 105 may be increased in size to incorporate passthrough 330 therein.

Figure 5:
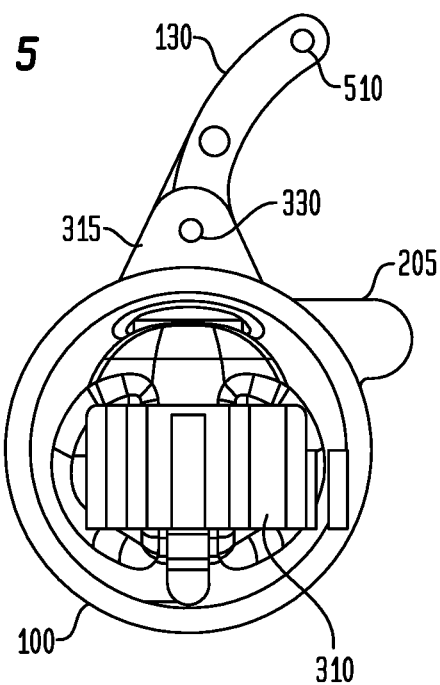
FIG. 5 illustrates a rear view of the first exemplary embodiment of the light management device shown in FIG. 1.

FIG. 5 illustrates a rear view of lighting device 100 showing a rear view of control section 130. In this illustrated view, control section 130 includes magnet 510. Magnet 510 provides a magnetic force, opposite that of the magnetic force of magnet 210. The opposing magnetic forces cause an attraction of magnet 510 to magnet 210 on housing extension 205 when magnet 510 is proximate to magnet 210. For example, magnet 510 may comprise a negative pole magnet that is attracted to a positive pole magnet 210. Alternatively, magnet 510 may comprise a positive pole magnet that is attracted to a negative pole magnet 210.

Although the retention of light management device 120 to housing 105 in an open (first) position, is one of magnet 510 and magnet 210, it would be recognized that magnet 510 need only be required when light management device 120 (or control section 130) is composed of a plastic or a non-magnetic metallic material (e.g., aluminum). However, when light management device 120, or at least lever 130, is composed of a magnetic material, magnet 510 may not be necessary.

As would be recognized, when control section 130 is positioned such that light management device 120 is in a first (open position, See FIG. 1), the magnetic forces of magnet 510 and magnet 210 attract to hold light management device 120 in the first position.

In accordance with the principles of the invention, an application of a force to one of control section 130 or light management device 120 sufficient to overcome the magnetic force attraction between magnets 510 and magnet 210 causes light management device 120 to change from the first (open) position to the second (closed) position (FIG. 2).

In accordance another aspect of the invention, light management device 120 may further comprise a cover extension 322 that extends substantially perpendicular, and conformal, to a second edge 145 (FIG. 1) of cover plate 122 of light management device 120, wherein cover extension 322 is configured to contact outer surface of housing 105 partially along a circumference of the distal end of housing 105. Cover extension 322, when light management device 120 is in the closed position, extends along the outer surface of housing 105 (which as illustrated is opposite that of stop channel 320). Cover extension 322 provides for a substantially light tight configuration with housing 105 when light management device 120 is placed in the closed position. Cover extension 322 provides for both the prevention of light being emitted between cover plate 122 and the distal end of housing 105 and for a limit of travel of light management device 120 during the transition from a first (open) position to a second (closed) position.

Figure 6:
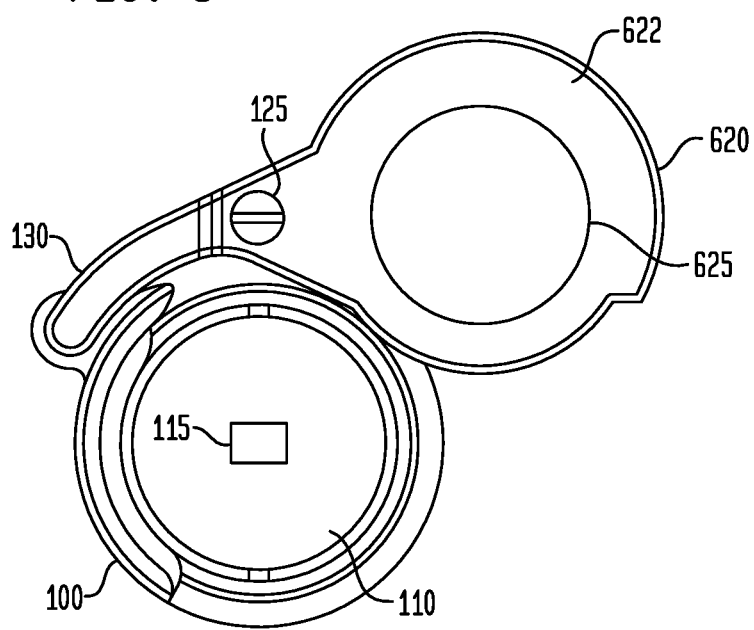
FIG. 6 illustrates front view of a second exemplary embodiment of a light management device shown in a first position.

FIG. 6 illustrates a front view of a second exemplary embodiment of light management system 600 incorporated onto a lighting device 100, which is suitable for being attached to a lighting assembly or a head mounting device such as eyewear, headband, headset, etc., in accordance with the principles of the invention.

In this illustrated embodiment, similar to FIG. 1, lighting device 100 includes a housing 105 that is closed on a first (or distal) end by lens 110 through which a light emitted by at least one lighting source 115 is viewable or projected onto an external surface. At least one lighting source 115 may be a Light Emitting Diode (LED) (i.e. lasing or non-lasing) that may emit light in at least one of a plurality of wavelength ranges. For example, when light in a UV light range is emitted, the user and those around the user, need protection from the harmful effects of the UV light, as previously discussed.

Further illustrated, is light management device 620 pivotally attached to housing 105 at pivot point 125, in a manner similar to that discussed with the light management device 120 disclosed in FIG. 1. For example, light management device 610 comprise a cover plate 622 and a control mechanism (e.g., lever) 130 that may be attached to housing 105 using a screw, pin or rivet 123 upon which light management device 620 pivots (or rotates) to change from a first position (shown) to a second position (see FIG. 7), as discussed with regard to FIGS. 1 and 2.

Further illustrated is lens/filter 625 incorporated into plate section 622. Lens 625 represents an optical filter that provides, in one aspect of the invention, for the reduction of a specified wavelength range of the light wavelengths emitted by at least one light source 115. For example, when at least one lighting source 115 outputs a UV light (e.g., wavelengths less than 500 nm), lens 625 may represent a UV blocking filter that prevents the transmission of UV light through filter 625. Thus, when lens/filter 625 is positioned in the second position, the viewing, or the projection, of UV light though filter 625 is reduced, block and/or inhibited.

Alternatively, when the at least one lighting source 115 outputs a broad band light containing UV light, lens 625 may be constructed to allow wavelengths that are not within the UV wavelength range (i.e., greater than 500 nm) to be passed while inhibiting wavelengths in the UV wavelength range (i.e., less than 500 nm). For example, when at least one lighting source 115 outputs a white light, then filter 625 may allow for the passage of light in a range not associated with UV wavelength ranges while allowing the remaining wavelengths to pass through. Thus, a visible light may be viewable through lens/filter 625 while UV wavelengths are attenuated or blocked by lens/filter 625.

Filter 625 may be an absorptive lens/filter or a reflective lens/filter that reduces the output of one or more designated wavelengths (e.g., UV light wavelengths) or wavelength ranges to an acceptable level.

Further illustrated is control section 130 which allows for the manipulation of light management device 620 from a first position (FIG. 6) to a second position (FIG. 7), by pivoting on pivot point 125 in a manner similar to that discussed with regard to FIGS. 1 and 2.

In one aspect of the invention, for example, in the dental arts, a dentist may utilize a white light source to view an operating area, when light management device 620 is in a closed position while blocking wavelengths in a wavelength range that is suitable for a curing operation, e.g., UV wavelength range. Thus, the practitioner may be able to view the operating area with a conventional light (that excludes UV light) and then allow the outputting of the UV light by altering the position of light management device 620 from a closed position to an open position.

In this aspect of the invention, the at least one lighting source 115 may comprise a first, white, light source and a second, curing, light source, wherein in a closed position, filter 625 blocks the output of the second, curing, light source while allowing the white light to passthrough. Alternatively, when filter 625 is positioned in an open position, light from both the first and second light sources may be projected onto the operating area, such that the dental material (or other similar material) may be cured using the output of the second, curing, light source.

Figure 7:
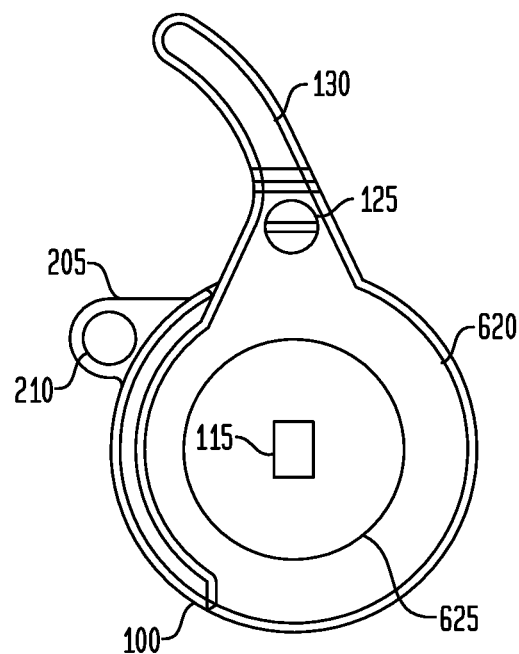
FIG. 7 illustrates a front view of the second exemplary embodiment of the light management device shown in FIG. 6 in a second position.

FIG. 7 illustrates a second frontal view of lighting device 100, wherein light management device 620 is placed in a second (closed) position such that light within a designated wavelength range (e.g., UV wavelength) emitted be lighting source 115 is blocked and/or alternatively, light emitted by lighting source 115, having wavelengths within a designated wavelength range, may be passed.

FIG. 7 further illustrates housing extension 205 including magnet 210 that is used to retain light management device 620 in an open position, in a manner similar to FIG. 2, discussed.

Figure 8:
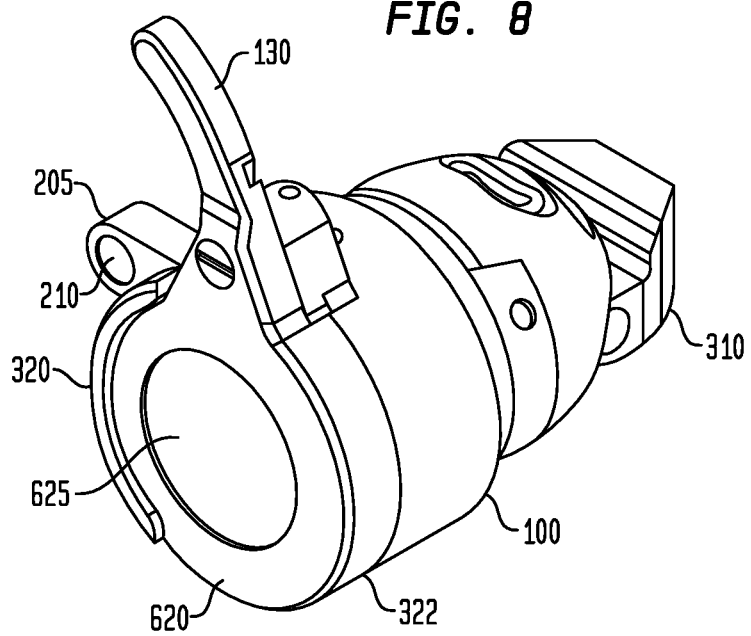
FIG. 8 illustrates a prospective view of the second exemplary embodiment of the light management device shown in FIG. 6.

FIG. 8 illustrates a prospective view of light device 100 including light management device 620 in a second position, which, as discussed, prevents the emission of light of a designated wavelength and/or allows the passage of light within a designated wavelength emitted from the at least one light source (i.e., LED) 115, as previously discussed.

As discussed with regard to FIG. 3, FIG. 8 illustrates stop channel 320 into which an edge of plate section 622 of light management device 620 fits. Stop channel 320 provides a means for retaining light management device 620 in a substantially light tight configuration, wherein light wavelengths cannot escape through cracks or slits between the light management device 620 and housing 105. Further illustrated is cover extension 322 that extends over the distal end of housing 105, as previously discussed. Cover extension 322, similar to stop channel 320, provides for a substantially light tight configuration when light management device 620 is placed in the closed position.

Figure 9:
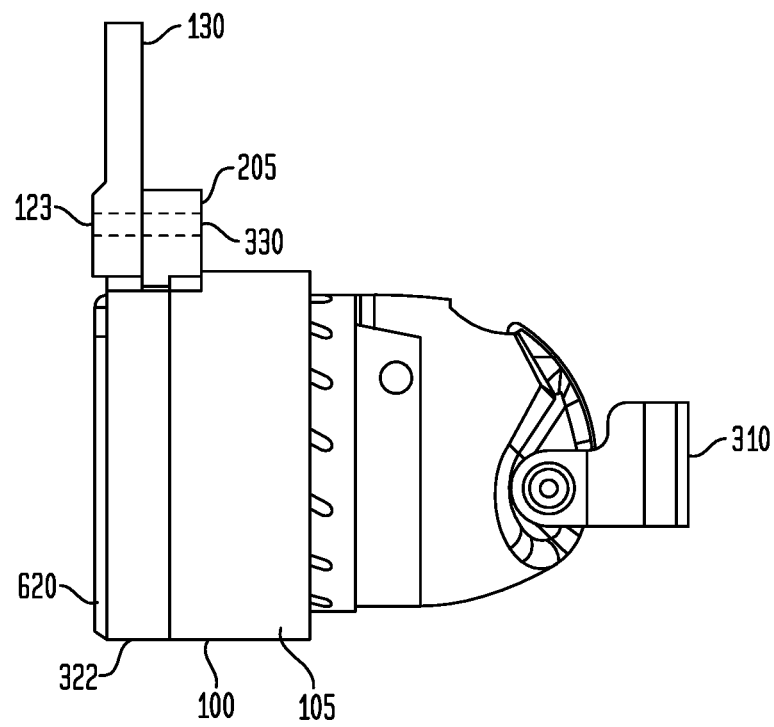
FIG. 9 illustrates a side view of the second exemplary embodiment of the light management device shown in FIG. 6.

FIG. 9 illustrates a side view of the lighting device 100 similar to the lighting device 100 shown in FIG. 6.

In this illustrated embodiment, the cover extension 322 fits tightly over the outer surface partially along the distal edge of housing 105 when light management device 620 is in a closed position. Further illustrated is attachment means 310 that allows for the attachment of lighting device 100 onto another element or device.

Figure 10:
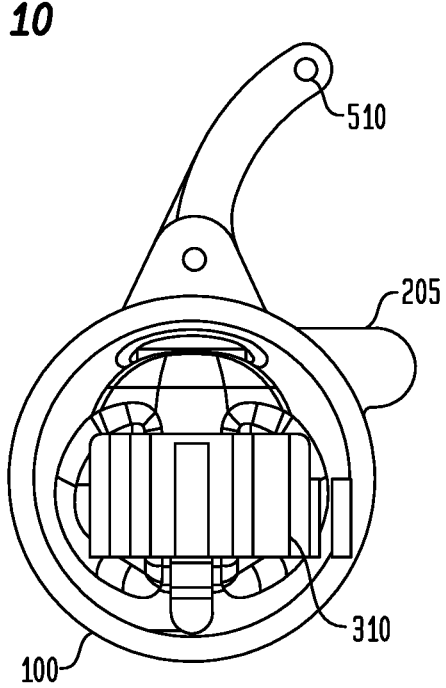
FIG. 10 illustrates a rear view of the second exemplary embodiment of the light management device shown in FIG. 6.

FIG. 10 illustrates a rear view of lighting device 100 showing magnet 510 on an end of control section 130, as previously discussed. Magnet 510 provides a magnetic force that interacts with a magnetic force of magnet 210 on housing extension 205. The magnetic force between magnets 510 and 210 retains light management device 620 in an open position, in a manner similar to that disclosed with regard to FIG. 5.

Although magnet 510 is shown, it would be recognized that magnet 510 may be required when light management device 620 (or lever 130) is composed of a plastic or a non-magnetic metallic material (e.g., aluminum). However, when at least control device 130 is composed of a magnetic material, magnet 510 may not be necessary.

As would be recognized, when control section 130 is positioned such that light management device 620 is in a first (open position, See FIG. 1, FIG. 6), the magnetic forces generated by magnet 510 and magnet 210 hold light management device 620 in the first (open) position. Application of a physical force to light management device 620, or to control section 130, sufficient to overcome the magnet force between magnets 510 and magnet 210, causes light management device 620 to change from the open position (FIG. 6) to the closed position (FIG. 7).

In accordance with the principles of the invention, when power, from an electrical source, such as a battery (not shown), is applied to the at least one lighting source 115, the light outputted by the at least one lighting source 115, when in the UV (or similar harmful wavelength range) may be blocked from being viewed by cover plate 120 or may be filtered by filter 625 when light management device 120/620 is in a closed position with regard to a distal end of housing 105. Similarly, in a case where the at least one lighting source 115 comprises two LEDs, one in the visible light wavelength range and the second in a harmful (e.g., UV) wavelength range, the light associated with the harmful wavelength range may be blocked by filter 625 associated with light management device 620 from being viewed or projected onto an external surface. In this case, visible light may be viewed while harmful wavelengths in the UV wavelength range may be prevented from being viewed Thus, the practitioner, with the opening of light management device 120 (620) is able to determine when light is viewable (or is outputted) from the at least one lighting device 115. Control of when light is viewable is advantageous as it provides the practitioner a means for controlling when light wavelengths in a harmful wavelength range (e.g., less than 500 nm) is projected onto an external surface. Further, it provides other personnel the ability to determine when harmful wavelengths are being emitted by their observing the position of light management device 120 (620).

Figure 11A:
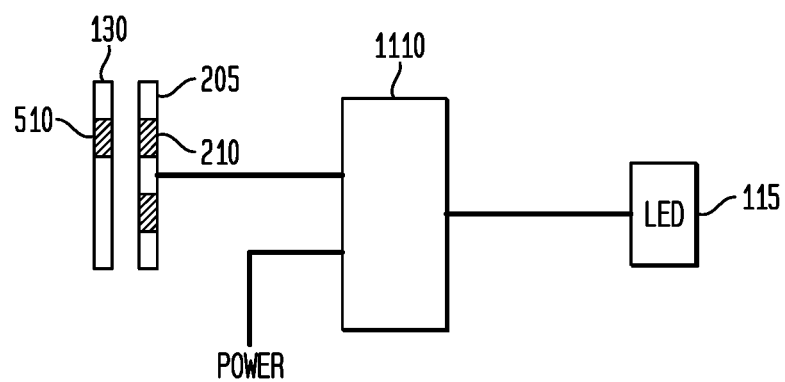
FIG. 11A illustrates a first exemplary circuit configuration of a light management system for controlling the output of a light source in accordance with the principles of the invention

FIG. 11A illustrates an exemplary embodiment of the light management device in accordance with an aspect of the invention, wherein control of the output of light from lighting source (e.g., LED) 115 (see FIG. 1, 6) may be determined by the position of light management device 120 (620). In one aspect, when light management device 120 (620) is in an open position, magnets 210 and 510 are positioned proximate to each other and thus, a signal may be generated indicating the proximate state of magnets 210, 510. The signal may be applied to circuit 1110, to which a power signal (e.g., a DC voltage value) may be concurrently applied. Power may be provided through a battery or AC/DC convertor (not shown). The presence of the signal indicating a proximate state of magnets 210, 510 causes power to be applied to lighting source 115. For example, the signal indicating proximity of magnet 510 with magnet 201 may be applied to an electronic switch (e.g., a power transistor), that allows power to be applied to, or removed from, at least one light source 115.

Hence, the user, having taken an action (i.e. moving light management device 120/620 into an open position) causes lighting source 115 to be powered, such that lighting source 115 may emit light (e.g., a UV light, a visible light or an Infra-Red light).

Circuit 1110 may comprise a power transistor (or switch) into which the signal indicating proximality of magnets 210/510 may operate to turn the power transistor 1110 to an ON position. In the ON position, power provided by the power source (not shown) is provided to lighting source 115.

Figure 11B:
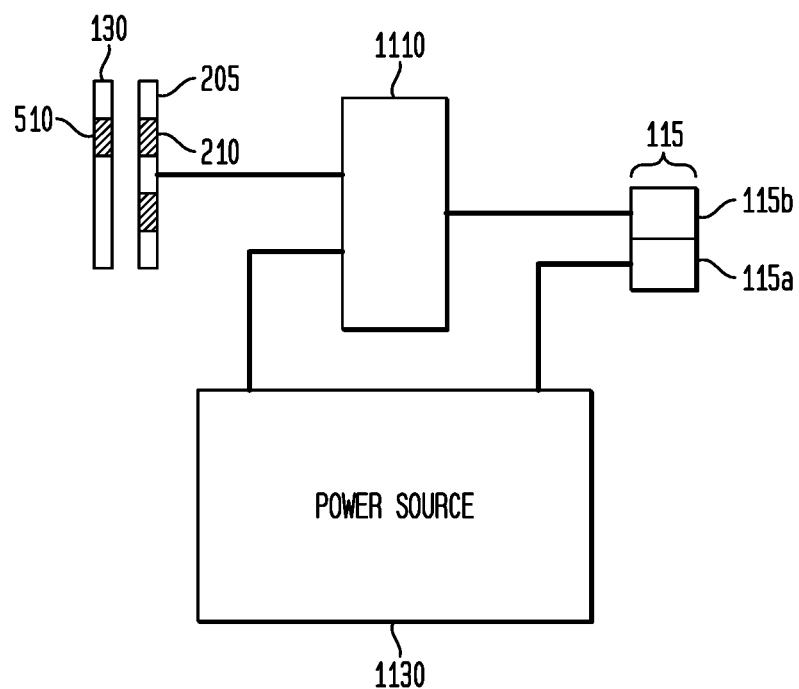
FIG. 11B illustrates a second exemplary circuit configuration of a light management system for controlling the output of a light source in accordance with the principles of the invention.

FIG. 11B illustrates a block diagram of a control circuit, in accordance with another aspect of the invention, for applying power continuously to an illumination LED (e.g., a white light) 115a and a control circuit, similar to that shown in FIG. 11A, that causes power to be applied to LED 115b selectively.

In this illustrated case, the at least one lighting source 115 is composed of two light sources (e.g., LED), wherein LED 115a may be configured to emit a visible wavelength and LED 115b may be configured to emit a second wavelength that may be considered a harmful wavelength. In this illustrated example, power provided by a power source 1130 may be applied directly to LED 115a, such that LED 115a is powered and emits light. Whereas, power may be applied to LED 115b, through switch 1110 only after magnet 210 and 510 are indicated to be proximate to one another.

Accordingly, when power, from a battery pack or AC/DC convertor 1130 is available, light from the white light source LED 115a is emitted, while light from lighting source 115b is not emitted. However, when cover (light management system) 620 is raised to an open position (and magnets 510 and 210 are proximate to one another) a signal may be generated to power switch 1110 that allows power to be provided to LED 115b.

Although, the control circuits discloses in FIGS. 11A and 11B, teach the application of a voltage or power from a power source 1130 under certain conditions of the light management system, it would be recognized that under the light management device disclosed, power may be applied at all times to the at least one light source 115, and that the viewability of the light generated by the power-ed ON at least one lighting source 115 outside of housing 105 may be controlled by the positioning of the light management system 120 (620) in one of an open or closed position.

Figure 12A:
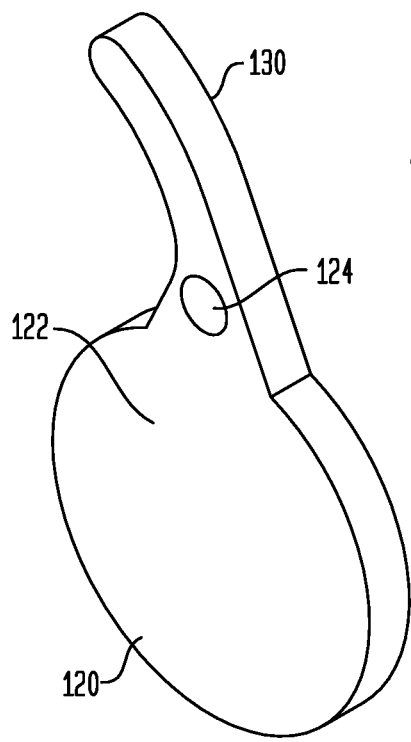
FIGS. 12A and 12B illustrate prospective views of exemplary embodiments of an exemplary light blocking cap of the light management system in accordance with the principles of the invention.

FIG. 12A illustrates a prospective view of a first exemplary embodiment the light management device in accordance with the principles of the invention.

In this illustrated first embodiment light management device 120 comprises a protective cap, presented as an opaque plate. 122 that blocks light emitted by the at least one lighting source 115, as shown in FIGS. 4 and 9, when the plate or cap 122 is retained in the blocking (or closed) position, as shown in FIG. 2. In this case, the protective light cap 122 operates as a shutter that slides (or pivots) from a first position to a second position over the distal end of housing 105 to cover lens 110 and prevent light emitted by the at least one lighting source 115 from exiting housing 105.

Figure 12B:
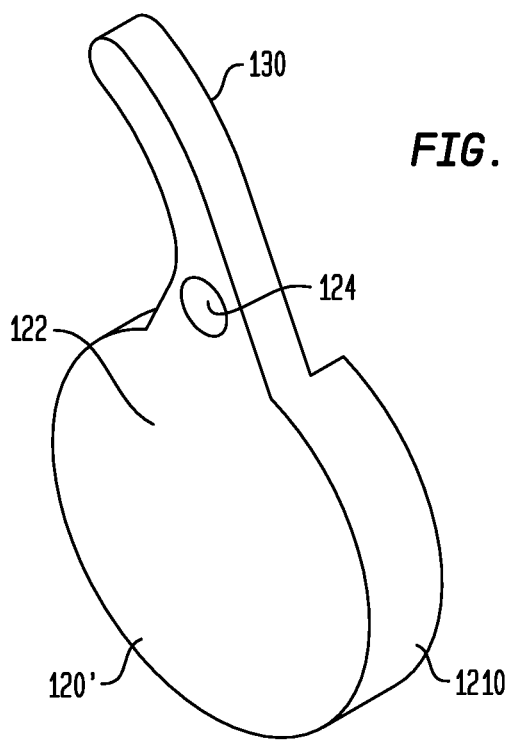

FIG. 12B illustrates a prospective view of a second exemplary embodiment of light management device in accordance with the principles of the invention.

In this illustrated second embodiment the light management system 120 (denoted as 120') is presented as a plate or cap 122 including a partial circumferential extension 1210 substantially perpendicular to plate 122. The circumferential extension 1210 is comparable to extension 322, previously discussed.

Extension 1210 is sized to contact an outer surface of housing 105 when cap 122 is retained in the blocking (closed) position, as shown in FIG. 2. In this case, extension 1210 contacts the outer surface of housing 105 to prevent or reduce the potential of light being emitted through a spacing between the distal end of housing 105 and the protective cap.

Although the light management devices (i.e., protective light cover, protective light cap, or light blocking cover) shown in FIGS. 12A and 12B are comparable to the light cover shown in FIG. 1, it would be recognized that the opaque cap 120 illustrated may similarly include a lens to filter the light emitted by the at least one lighting source 115 as shown in FIG. 6, for example.

In another aspect of the invention, although a magnetic connection between housing 105 and light management device 120 (620) is shown in housing extension 210, it would be appreciated that the position of the magnetic connection between housing 105 and light management device 120 (620) may be altered without altering the scope of the invention. For example, magnet 210 associated with housing 105 may be positioned on a surface of housing 105 and magnet 510 may be positioned on light management device 120 1(620) in a position corresponding to magnet 210 such that light management device 120 (620) is held in place by the magnetic forces between magnets 210 and 510.

In accordance with another aspect of the invention, light management device 120 (or 620) may be spring loaded, such that light management device 120 (or 620) is forced into a closed position when magnet 510 is not proximate to magnet 210. That is, the magnetic force between magnets 510 and 210 is sufficient to retain light management device 120 (or 620) in an open position. However, a force applied to one of control section 130 or light management device 120 (or 620) may cause a change in the position of magnet 510 with respect to magnet 210 into a closed position, wherein a spring provides additional force that aids the movement of light management device 120 (620) from the open position to the closed positioned.

In accordance with another aspect of the invention, light management device 120 (620) may comprise a ball and socket connection, wherein magnet 210 may be replaced by a ball or sphere embedded within housing extension 205. Similarly, magnet 510 may be replaced by a socket or indentation within control means 130, wherein the indentation may engage the ball or sphere in housing extension 205 to retain light management device 120 (620) in an open position.

Figure 13:
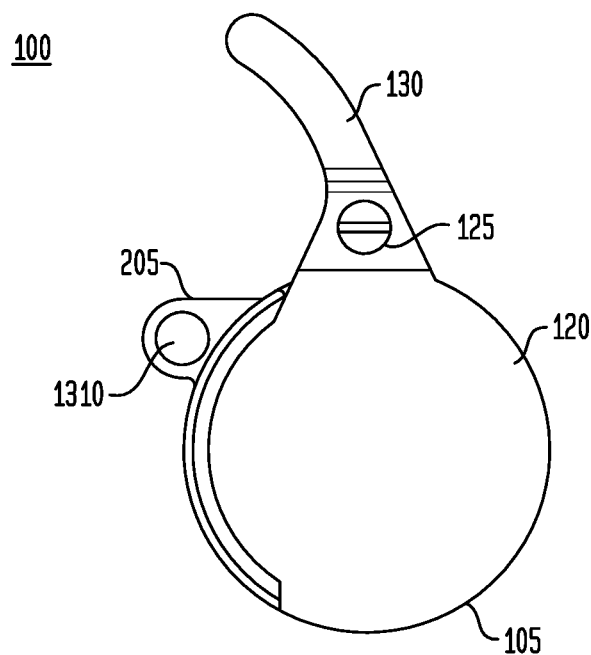
FIG. 13 illustrates a front view of a third exemplary embodiment of a light management device shown in a first position in accordance with the principles of the invention.

FIG. 13 illustrates a front view of a third exemplary embodiment of a light management device 120 in accordance with the principles of the invention.

In this exemplary embodiment, a ball and socket connection is utilized to retain light management device 120 (620) in an open position. In this illustrated case, which shows light management device 120 in a closed position, a ball or spherical shaped object 1310 is incorporated into housing extension 205. Ball or spherical shaped object 1310 extends from housing extension 205 such that a portion (typically about one half) of ball 1310 is retained within housing extension 205. Illustrated light management device 120/620, similar to FIG. 1, is held in place when an indentation within control section 130 is positioned proximate to housing extension 205 such that the extended section of ball or spherical shaped object 1310 engages indentation on control mechanism 130.

Figure 14:
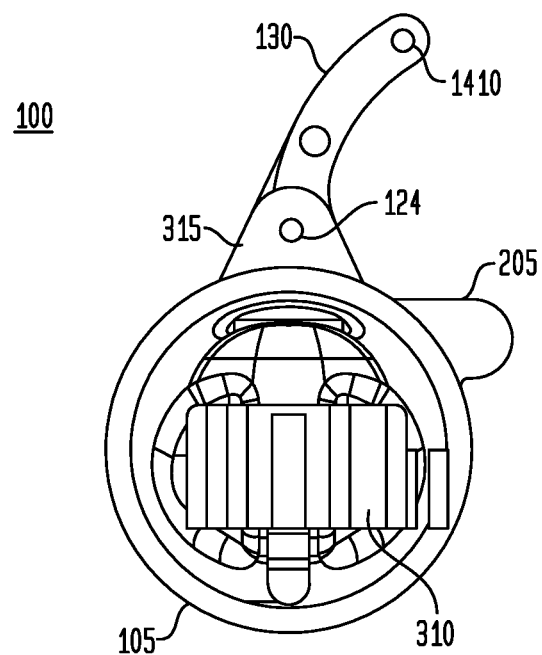
FIG. 14 illustrates a rear view of the third exemplary embodiment of the light management device shown in FIG. 13.

FIG. 14 illustrates a rear view of the third exemplary embodiment of light protection cover shown in FIG. 13.

In this illustrated embodiment, control section 130 includes indentation 1410, which when proximate to ball 1310 captures the extended portion of ball or sphere 1310, therein.

In this third exemplary embodiment, a force applied to light management device 120/620 or control section 130 dislodges the extended portion of ball 1310 from indentation 1410 to allow light management device 120/620 to pivot about pivot point 125 to cause light management device 120/620 to change from an open position (e.g., FIG. 1) to a closed position (e.g., FIG. 2). Although not shown, it would be appreciated that a spring mechanism may be incorporated such that the spring mechanism may provide addition force to aid the movement of light management device 120/620 from the open position to the closed position.

Although a ball and sphere configuration is illustrated and disclosed, other physical retention methods may be incorporated into the invention discussed, herein, without altering the scope of the invention. For example, lever 130 may include the spherical or ball 1310 while indentation 1410 may be incorporated into housing extension 205. In another embodiment, control section 130 may be held in place by a physical connection such as a pin captured by a hook extending from housing extension 205.

As would be understood, a force may be applied to control section 130 to raise light management device 120 (620) from the closed position to the open position. Once in the open position, the magnetic attraction between magnets 510 and 210 becomes sufficient to retain light management device 120 (620) in the open position, as previously discussed.

Figure 15:
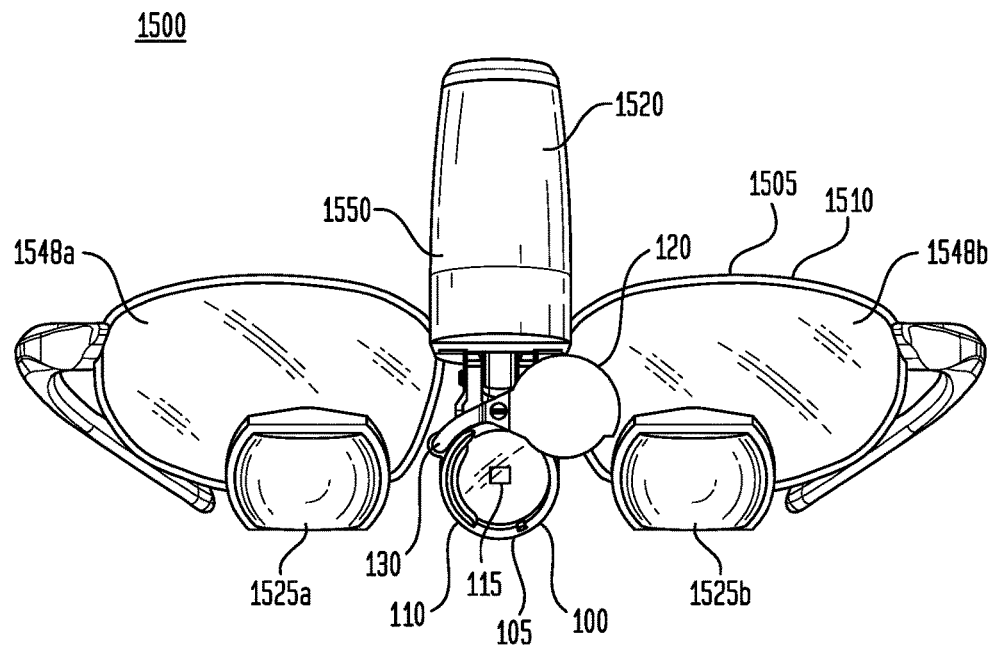
FIG. 15 illustrates a front view of an exemplary application of the light management device in accordance with the principles of the invention.

FIG. 15 illustrates a front view of an exemplary eyewear application 1500 incorporating a lighting device 100 with light management device 120 in accordance with the principles of the invention.

Exemplary eyewear application 1500 comprises a eyewear frame 1510 comprising frame 1505 into which lens 1548 (of which left and right lens are labelled 1548a, 1548b, respectively) are retained. Left and right lens 1548a, 1548b may be ordinary glass or may be prescriptive glass. Left and right lens 1548a, 1548b may further be clear or tinted, wherein the tinting may be used to protect the user's eyes from stray light that may be damaging to the user. Eyewear frame 1510 may also be a headband or a headset (not shown), which are well-known devices (i.e., means) for attaching the telescopic lens and/or lighting elements to a user. Also illustrated are telescopic lens 1525a, 1525b attached to corresponding left and right lens, 1548a, 1548b, respectively.

Further illustrated is headlight assembly 1550 attached to frame 1505 of an eyewear 1500. Headlight assembly 1550 comprises a housing 105 including, therein, at least one lighting source 115 and a lens 110 positioned at a distal end of housing 105. Further illustrated is light management system 120 disclosed, for example, in FIG. 1, positioned along a distal end of housing 105 in a first position, wherein light emitted by at least one light source 115 contained within housing 105 may be projected onto an external surface (or viewable by a user standing opposite the distal end of housing 105).

In this illustrated application of the light management system 120 disclosed in FIG. 1, for example, housing 105 (and the lighting source contained therein) is oriented at a depression angle (with respect to a horizontal light through eyewear 1500 similar to that of the angle of telescopic lens 1525 (labelled left 1525a and right 1525b, respectively). The orientation of housing 105 with respect to the orientation of telescopic lens 1525 is advantageous as it allows for the direction of light generated by the at least one lighting source (e.g., LED) 115 to an area that is substantially convergent with a focal point of telescopic lens 1525a, 1525b.

As discussed, the light management system 120, selectively inhibits (blocks, FIG. 1) or filters (FIG. 6) light emitted by the at least one lighting source 115 contained in the housing 105. As discussed, the position of light management device 120 (620) determines whether light emitted by the at least one lighting source 115 is projected onto an external surface.

Further illustrated is pod 1520 containing a power source (e.g., a battery) that is used to power the at least one lighting source 115 within housing 105 and other electronic circuitry (not shown) that is used to control a voltage (or current), supplied by the power source, applied to the lighting source.

For example, the (not shown) electronic circuitry may be configured to allow for a capacitive touch of a metallic element on pod 1520 to turn on/turn off the voltage or current applied to at least one lighting source 115. (see for example, U.S. Pat. No. 10,352,543, the contents of which are incorporated by reference, herein). In another aspect of the invention, the electronic circuitry may be configured to allow for a non-contact control of the voltage (or current) applied to lighting source 115. Non-contact control of the voltage (or current) may be achieved by the occurrence of a detection of a reflection of a transmitted signal. In one aspect, a signal (infra-red, ultra-sonic, etc.) may be transmitted through a transmitter (not shown) that is reflected by an object. A reflection of the transmitted signal may be detected by a receiver (or a detector) (not shown). The receiver or detector may then generate an indication of the reflected signal, to which the electronic circuitry, in response to the indication of the reflected signal, may turn on the at least one lighting source 115 or turn off the at least one lighting source 115. (see for example, U.S. Pat. No. 9,791,138, the contents of which are incorporated by reference, herein.)

As would be appreciated, the control and application of power (i.e., voltage and/or current) to the at least one lighting source 115 discussed, may be integrated with, or separate from, the power control disclosed with regard to FIGS. 11A and 11B.

Although the power source is shown attached to the exemplary eyewear 1500, in the illustrated exemplary application of the light management device 120, disclosed, herein, it would be recognized that the power source may be separated from the eyewear and those skilled in the art would have the knowledge to alter the configuration shown to provide an external power source and to provide power from such external power source lighting source 115 without undue experimentation. (see for example, U.S. Pat. No. 8,851,709, the contents of which are incorporated by reference, herein).

Further illustrated is light management device 120 held in an open position, as discussed with regard to FIG. 1, for example. In this illustrated example, light emitted by light source 115 is viewable (assuming visible light) by persons utilizing the eyewear 1500 or by persons opposite eyewear 1500. As discussed, when light source 115 emits light that is hazardous to the eyes of persons who may view the emitted light, a user may determine when such hazardous light may be viewable by placing light management device 120 in the illustrated open position. Otherwise, by retaining light management device 120 in a closed position, the light emitted by the at least one light source 115 is either not viewable outside of housing 105 (FIG. 1) or filtered viewable outside of housing 105 (FIG. 6). Hence, harmful light emitted by the at least one light source 115 cannot be inadvertently viewed by persons.

Figure 16:
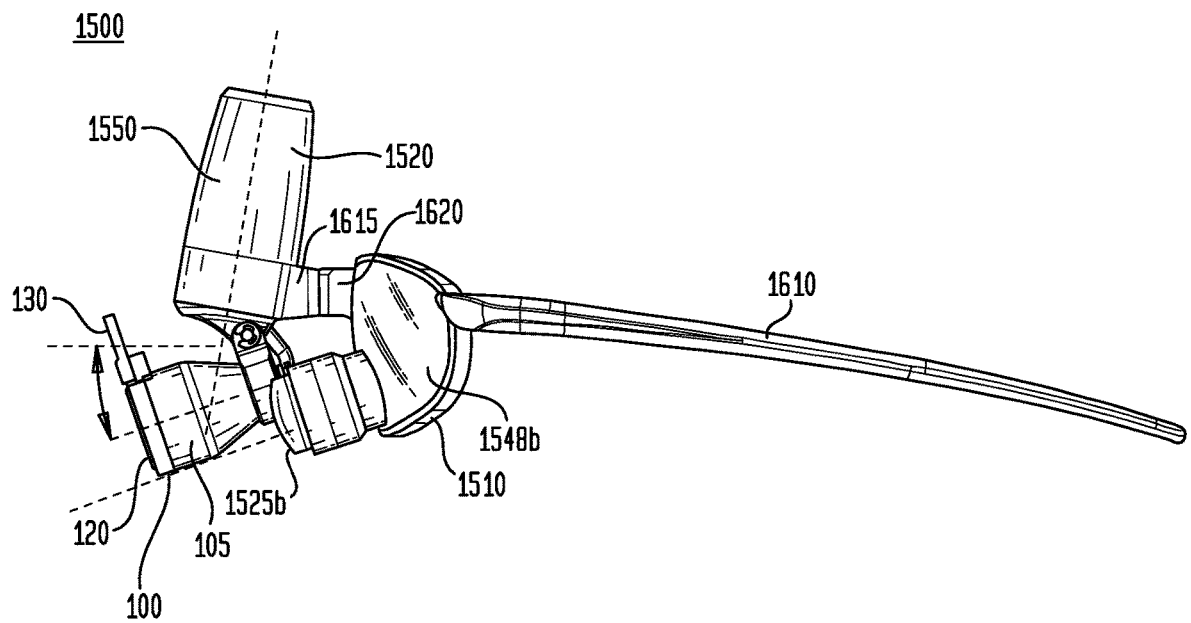
FIG. 16 illustrates a side view of the exemplary application of the light management device shown in FIG. 15.

FIG. 16 illustrates a side view of the exemplary powered headlight assembly 1500 shown in FIG. 15.

In this illustrated embodiment, eyewear 1500 includes frame 1505 and temple 1610. Temple 1610 provides a conventional means for retaining eyewear 1500 in place on a user's head. Although not shown it would be recognized that the headlight assembly 1550 including pod 1520 and housing 105 may be attached to a headband or headset or to a user's clothing or an external stand device without altering the scope of the invention.

Also, shown is mating connector 1620 attached to frame 1605. Mating connector 1620 is positioned between lens 1548a, 1548b. to retain headlight assembly 1550 substantially centered with regard to eyewear 1500.

Also shown is connector 1615, on headlight assembly 1550, attached to mating connector 1620. Connector 1615 and mating connector 1620 may be T-slot connectors that allow headlight assembly 1550 to be removable from eyewear 1510. In another aspect of the invention, connector 1615 and 1620 may provide for a fixed attachment, wherein the connectors 1615 and 1620 are a single unit.

Although connector 1615 is shown extending from headlight assembly 1550, it would be recognized that connector 1615 may be comparable to the attachment section 310 shown in FIG. 3, for example. Thus, lighting device 100 may operate independently of eyewear shown in FIGS. 15 and 16.

Further illustrated is lens or light management device 120 (or 620) positioned in front of housing 105 (i.e., a closed position). As discussed, in this position light emitted by the at least one light source 115 may be inhibited from exiting housing 105 or may be filtered prior to exiting housing 105.

Figure 17:
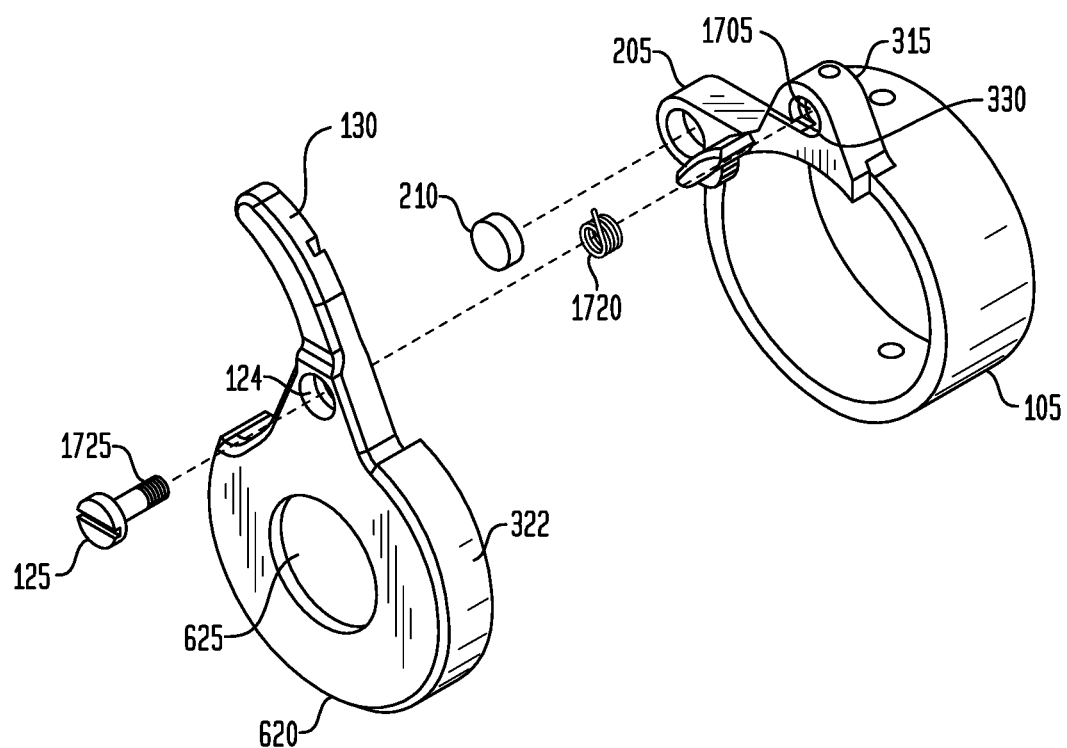
FIG. 17 illustrates an expanded perspective view of the exemplary embodiment of the light management device shown in FIG. 8.

FIG. 17 illustrates an exploded perspective of the configuration of the light management system shown in FIG. 8.

In this illustrated example, light management device 620 includes filter 625, cover extension 322 control mechanism (e.g. lever) 130, as previously discussed.

Further shown is passthrough 124 between cover plate 622 and lever 130. Passthrough 124 allows for a connection means 125 to passthrough light management device 620 so as to retain light management device 620 onto housing 105. Furthermore housing 105 includes attachment section 315 and housing extension 205, into which magnet 210 that may be inserted.

In this illustrated exemplary aspect of the invention, connection means 125 is represented as a screw connector including a screw thread 1725. Attachment section 315 further includes an internal screw thread 1705.

Accordingly, light management device 120/620 may be retained onto a distal end of housing 105 by the insertion of screw 125 through passthrough 124 to engage screw thread 1725 within attachment section 315.

Further illustrated is spring 1720 through which connection means (e.g., screw 125) may pass. Spring 1720 may represent a torsion spring, for example, which is under compression when light management device 120/620 is in an open position.

In this case, the magnetic force between magnets 210 and 510 is greater than the force applied by spring 1720. However, when a force is applied to control mechanism 130, the unwinding of torsion spring 1710 or the release of the tension force of spring 1710 provides an extra force to aid the movement of light management device 120/620 from the open position to the closed position.

In summation, a light management system is disclosed that includes a protective light cap or cover that provides for the blockage of designated wavelengths or the allowance of designated wavelengths from being inadvertently viewed by persons. The light management device comprising a protective light cap or cover, that is pivotably connected to a housing containing at least one lighting source, therein, to allow the cap to be positioned over the at least one light source to block or selectively block (or filter) light emitted from the at least one light source from exiting the housing. The protective light management device operates in one of an open position that allows emitted light to be projected onto an external surface or in a closed position that inhibits emitted light from being projected onto an external surface. The protective light management device is held is the open position by, preferably, a magnetic connection between the light management device and the housing.

Although the invention has been described with regard an LED lighting source, it would be recognized that the term "a LED" is a term of art and refers to a lighting element and it would be understood that other lighting sources may be incorporated into the invention disclosed without undue modification and, thus, considered within the scope of the invention claimed.

One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention. Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure.

It is expressly intended that all combinations of those elements that perform substantially the same function in substantially the same way to achieve the same results are within the scope of the invention. Substitutions of elements from one described embodiment to another are also fully intended and contemplated.

What is claimed is:

1. A lighting element comprising:
   a housing comprising:
      at least one lighting source therein;
      a lens positioned on a distal end of said housing; and
      an attachment section extending from said housing;
   a light management system positioned adjacent the distal end of the housing, said light management system comprising:
      a light protective cap comprising:
         a front plate sized comparable to said distal end of said housing;
         a control section extending from said front plate; and
         a passthrough positioned between said front plate and said control section; and
      a cylindrical shaped object extending through said passthrough, wherein said cylindrical shaped object is configured to:
         engage said attachment section to
         retain said light protective cap to said housing, wherein said front plate is configured to:

pivot about said cylindrical shaped object from a first position in which said front plate is positioned away from said distal end to a second position in which said front plate is positioned in front of said distal end, wherein said housing comprises:
means to retain said light management system in said first position.

2. The lighting element of claim 1, wherein said cylindrical shaped object is one of: a screw, a pin and a rivet.

3. The lighting element of claim 1, wherein said attachment extension comprises a passthrough, and said cylindrical shaped object is configured to:
engage said attachment extension passthrough to retain said light management system to said housing.

4. The lighting element of claim 1, wherein said distal end of said housing comprises:
a channel extending partially around a circumference of said distal end.

5. The lighting element of claim 1, wherein said front plate comprises:
a plate extension extending substantially perpendicular to said front plate, said plate extender configured to:
contact an outer surface of said housing partially around a circumference of said distal end of said housing.

6. The lighting element of claim 1, wherein said means for retaining said light management system in said first position comprises:
a first magnet, contained within a housing extension attached to said housing, said housing extension extending substantially perpendicular to said attachment section, wherein said first magnet exerts a magnetic force on said control section.

7. The lighting element of claim 1, wherein said front plate comprises:
a filter, said filter configured to block light emitted by said at least one lighting element from exiting said housing.

8. The lighting element of claim 1, wherein said front plate comprises:
a filter, said filter configured to:
allow passage of light of a designated wavelength range emitted by said at least one lighting source to exit from said housing; and
block passage of light of a second designated wavelength range emitted by said at least one lighting source from exiting said housing.

9. The lighting element of claim 1, wherein said at least one lighting source comprises at least one lighting source emitting light in at least one of: an ultraviolet wavelength range, a visible wavelength range and an Infra-Red wavelength range.

10. The lighting element of claim 1, wherein said light protective cap is configured to block all light emitted by the at least one lighting source.

11. The lighting element of claim 1, wherein said at least one lighting source comprises at least one of: a lasing source and a non-lasing source.

12. The lighting element of claim 3, wherein said attachment section passthrough is one of: threaded and smooth, wherein said smooth passthrough comprises one of: a snap fit, a force fit, and a pressure fit connection.

13. The lighting element of claim 3, wherein said means for retaining said light management system in said first position comprises:
a spherical element partially extending from a housing extension attached to said housing, said housing extension extending substantially perpendicular to said attachment section; and
an indentation within said control section, wherein said indentation is aligned to said spherical element when said protective cap is in said first position.

14. The lighting element of claim 6, comprising:
a second magnet attached to said control section, wherein said second magnet is aligned to said first magnet when said light protective cap is in said first position.

15. The lighting element of claim 7, wherein said filter is configured to block light emitted in a wavelength range less than 500 nm.

16. The lighting element of claim 8, wherein said filter is configured to block the passage of light emitted in a wavelength range less than 500 nm and pass light in a wavelength range greater than 500 nm.

17. A lighting device comprising:
a battery configured to output a voltage;
a switch configured to receive said voltage;
a lighting element comprising:
a housing comprising:
an attachment section extending from said housing;
a housing extension extending from said housing, said housing extension positioned substantially perpendicular to said attachment section;
at least one lighting source, wherein said voltage is selectively applied to said at least one lighting source by said switch; and
a lens positioned on a distal end of said housing;
a light management device positioned adjacent to the distal end of the housing, said light management system comprising:
a light protective cap comprising:
a plate sized comparable to said distal end of said housing;
a control section extending from said plate; and
a passthrough positioned between said plate and said control section; and
a cylindrical shaped object extending through said passthrough, said cylindrical shaped object configured to:
engage said attachment section, and
attach said light management device to said housing, wherein said light protective cap is configured to:
pivot about said cylindrical shaped object from a position away from said distal end to a position in front of said distal end.

18. The lighting device of claim 17, wherein said light protection cap comprises:
a filter, said filter configured to block light emitted within a predetermined wavelength range.

19. The lighting device of claim 17, wherein said attachment section comprising:
a passthrough, said passthrough configured to engage said cylindrical shaped object.

20. The lighting device of claim 17, wherein said light management device comprising:
a first magnet positioned on said control section: and
a second magnet positioned within said housing extension, wherein said first magnet and said second magnet align when said light protective cap is positioned away from said distal end.

* * * * *